United States Patent [19]

Marx

[11] 3,965,181
[45] June 22, 1976

[54] TRICYCLIC PHARMACOLOGICAL AGENTS, INTERMEDIATES AND METHODS OF MAKING

[75] Inventor: Michael Marx, Sunnyvale, Calif.

[73] Assignee: Syntex (U.S.A.) Inc., Palo Alto, Calif.

[22] Filed: May 1, 1975

[21] Appl. No.: 573,495

Related U.S. Application Data

[63] Continuation of Ser. No. 377,107, July 6, 1973, abandoned.

[52] U.S. Cl. .................. 260/570.8 TC; 260/239 B; 260/240 TC; 260/465 E; 260/465 K; 260/556 AR; 260/611 F; 260/618 F; 260/456 R; 424/246; 424/248; 424/250; 424/256; 424/263; 424/270; 424/273; 424/274; 424/303; 424/304; 424/325; 424/339; 424/340; 424/343
[51] Int. Cl.² ........................................ C07C 87/29
[58] Field of Search ............ 260/240 TC, 570.8 TC, 260/465 E, 465 K

[56] References Cited
UNITED STATES PATENTS

| 2,985,660 | 5/1961 | Judd et al. ..................... 260/293.62 |
| 3,073,847 | 1/1963 | Doebel ............................... 260/328 |
| 3,126,411 | 3/1964 | Rey-Bellet et al. .............. 260/570.8 |
| 3,270,067 | 8/1966 | Wendler ......................... 260/649 R |
| 3,272,864 | 9/1966 | Hoffsommer et al. ........... 260/570.8 |
| 3,384,663 | 5/1968 | Rey-Bellet et al. ............ 260/240 TC |
| 3,409,640 | 11/1968 | Villani ......................... 260/240 TC |
| 3,547,998 | 12/1970 | Lacefield .................. 260/570.8 TC |
| 3,819,723 | 6/1974 | Dvolaitzky et al. ........ 260/570.5 CA |
| 3,828,034 | 8/1974 | Marx et al. ................. 260/570.8 TC |
| 3,849,410 | 11/1974 | Nakanishi et al. ............ 260/240 TC |
| 3,862,131 | 1/1975 | Beck et al. ................. 260/570.8 TC |

FOREIGN PATENTS OR APPLICATIONS

| 577,057 | 4/1959 | Belgium |
| 609,095 | 10/1962 | Belgium |
| 578,122 | 5/1959 | Belgium |
| 582,220 | 2/1960 | Belgium |
| 589,192 | 5/1960 | Belgium |

OTHER PUBLICATIONS

Mychajlyszyn et al., 1959, Coll. Czeck Chem. Commun., 24, 3955.
Protiva et al., J. Med. Pharm. Chem., 4 (1961), p. 411.
Villani et al., J. Med. Pharm. Chem., 5 (1962), p. 373.
Winthrop et al., J. Org. Chem., 27 (1962), p. 230.
Gordon, Psychopharmacological Agents, Academic Press, N.Y., N.Y., 1964, pp. 68–71.

Primary Examiner—Arthur P. Demers
Attorney, Agent, or Firm—Lawrence S. Squires; William B. Walker

[57] ABSTRACT

5-(3-Substituted prop-cis-1-enyl)- and 5-(3-substituted prop-trans-1-enyl)- derivatives of 5H-dibenzo[a,d]cycloheptenes and 10,11-dihydro-5H-dibenzo[a,d]cycloheptenes and methods of making. The process of preparing the 5-(3-substituted prop-cis-1-enyl)- derivatives comprises hydrogenation of the appropriate 5-(3-substituted prop-1-ynyl)- derivatives in the presence of a noble metal catalyst. The 5-(3-substituted prop-trans-1-enyl)- derivatives can be prepared via treatment of the appropriate 5-(3-substituted prop-1-ynyl)- derivative with an alkali metal (e.g. sodium) in the presence of ammonia. Both the 5-(3-amino-cis- and 3-amino-substituted prop-trans-1-enyl)- derivatives exhibit antihistamine activity and are further useful in the treatment of, and/or palliation of, abnormal conditions occurring in mammals, related to the central nervous system. The remaining compounds have utility as intermediates for pharmacologically active compounds.

7 Claims, No Drawings

TRICYCLIC PHARMACOLOGICAL AGENTS, INTERMEDIATES AND METHODS OF MAKING

CROSS REFERENCE TO RELATED APPLICATION

This application is a continuation of Ser. No. 377,107, filed July 6, 1973 now abandoned.

BACKGROUND OF THE INVENTION

1. Field of the Invention

This invention relates to 5-(3-substituted prop-cis-1-enyl)- and 5-(3-substituted prop-trans-1-enyl)- derivatives of 5H-dibenzo[a,d]cycloheptenes and 10,11-dihydro-5H-dibenzo[a,d]cycloheptenes and to methods of preparing such derivatives. In a further aspect, this invention relates to 5-(3-substituted aminoprop-cis-1-enyl)- derivatives of 5H-dibenzo[a,d]cycloheptenes and 10,11-dihydro-5H-dibenzo[a,d]cycloheptenes, and to methods of preparing such derivatives. In a still further aspect this invention relates to 5-(3-substituted aminoprop-trans-1-enyl)- derivatives of 5H-dibenzo[a,d]cycloheptenes and 10,11-dihydro-5H-dibenzo[a,d]cycloheptenes and to methods of preparing such compounds. In another aspect, this invention relates to 5-(3-hydroxypropcis-1-enyl)- derivatives of 5H-dibenzo[a,d]cycloheptenes and 10,11-dihydro-5H-dibenzo[a,d]cycloheptenes and ethers and alkylsulfonyl esters thereof and 5-(3-hydroxyprop-trans-1-enyl)- derivatives of 5H-dibenzo[a,d]cycloheptene and 10,11-dihydro-5H-dibenzo[a,d]cycloheptene and ethers and alkylsulfonyl esters thereof and to methods of preparing such derivatives, ethers and alkylsulfonyl esters.

2. The Prior Art

Within the past 15 years, significant advances have occurred within the field of chemotherapy, especially with respect to the treatment of mental depression. One family of compounds, which have been found to be particularly useful in the treatment of endogenous depression (also referred to as melancholic or involution depression) is the family comprising dibenzazepine and dibenzocycloheptene compounds. These compounds are characterized by two benzene rings joined together by a fused cycloheptane ring. The cycloheptane ring frequently contains at least one hetero constituent such as, for example, nitrogen in the dibenzazepines, and can optionally contain a double bond in the 2-carbon atom bridge linking the two benzene rings. A further discussion of this family of compounds, including their chemotherapeutic usefulness in the treatment of mental depression can be had by reference to the literature of the prior art such as, for example, Biel, J., "Chemopharmacologic Approaches to Mental Depression", *Drugs Affecting the Nervous System*, Edit., Burger; Vol. 2, pages 85–125, Marcel Dekker Corp., New York (1968); and Dale, J., "Some Rationales for the Development of Anti-Depressant Drugs", *Molecular Modification on Drug Design*, Advances in Chemistry Series, 45, pages 114–139, 129–136, American Chemical Society, Washington, D.C. (1964); and Klerman and Cole, "Clinical Pharmacology of Imipramine and Related Anti-Depressant Compounds", *Pharmacological Reviews*, Vol. 17, No. 2, pages 101–141 (1965).

The tricyclic anti-depressants, e.g. imipramine, amitriptyline, etc., have been found to possess the advantage that they exhibit strong anti-depressant activity in subjects suffering from endogenous depression, yet exhibit either no activity or only very mild sedative activity in normal subjects. This is particularly important because of the difficulty of clinically distinguishing true endogenous depressive patients from patients who are merely suffering a momentary period of depression. A further and major problem compounding the difficulty of treating endogenous depression is that endogenous depression is seldom a pure depression phenomenon. Typically, there is a dominated anxiety syndrome which can be released by palliation of the depression component. Thus, pure treatment of the depression component frequently results in replacement of the dominant depression manifestation with manifestation of agitation, hostility, belligerency or other undesirable anxieties. This problem is so typically encountered that anti-depressants such as imipramine are now frequently prescribed in combination with a tranquilizer. Therefore, it has become well recognized that an optimum agent for treating endogenous depression should possess not only strong anti-depressant properties selective to subjects suffering from endogenous depression as contrasted to normal subjects, but should also have the seemingly antithetical property of having moderate tranquilizing or sedative properties. Accordingly, we have now discovered compounds having the desired combination of anti-depressant and tranquilizing or sedative properties and which can be properly classified as true tranquilizing anti-depressants. In addition, we have discovered compounds having potent anti-depressant activities with insignificant or no tranquilizing activities, which can be classified as pure anti-depressants. Both classes of compounds further exhibit potent antihistamine properties and thus can also be used as antihistamines, preferably in reduced dosages.

SUMMARY OF THE INVENTION

In summary the compounds of our invention can be represented by the following generic formula:

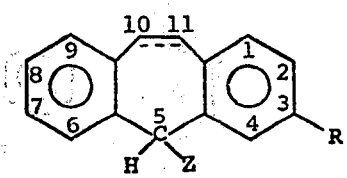

(I)

wherein the dotted line indicates either a saturated (ethylene) bridge or a double bond (vinyl) bridge between the C-10 and C-11 carbon atoms;

R is hydrogen, lower alkyl, lower alkoxy, lower alkenyl, trifluoromethyl, alkylsulfonyl, trifluoromethylsulfonyl, thioalkyl, dialkylsulfamoyl, or cyano;

Z is a group having the formulas:

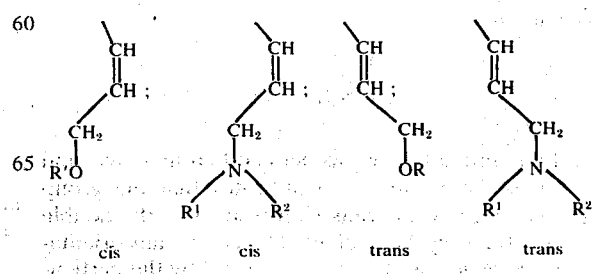

wherein —OR' is hydroxy, labile ether group or the group —OSO$_2$R$_2$' wherein R$_2$' is lower alkyl; and R$^1$ and R$^2$ are independently hydrogen, lower alkyl, lower cycloalkyl, phenylalkyl, phenacyl or substituted phenacyl; or R$^1$ and R$^2$ together with the nitrogen atom to which they are joined form a heterocyclic ring having from 5 through 7 ring atoms having from 1 or 2 hetero atoms selected from the group consisting of nitrogen, sulfur and oxygen, wherein one of said hetero atoms is the joining nitrogen atom, or R$^1$ and R$^2$ together with the nitrogen atom to which they are joined form a substituted nitrogen heterocyclic ring.

Also encompassed within our invention are pharmaceutically acceptable salts of the compounds of formula I.

In summary one process of our invention can be represented by the following schematic overall reaction equation:

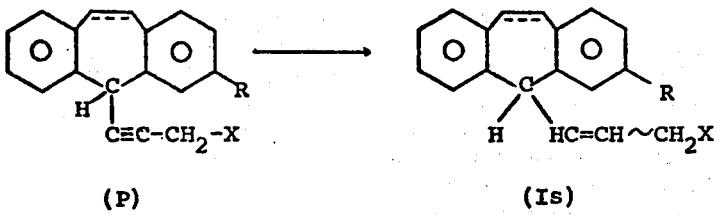

(P)        (Is)

wherein X is hydroxy, acid labile ether or the group

and wherein

R and the dotted line are as defined herein above, and wherein the wavy line (∼) indicates that the group CH$_2$X is either cis or trans with respect to the double bond and the tricyclic nucleus. The cis or trans orientation of the major product is determined by the particular process used to reduce the compounds of formula P to the compounds of formula (Is) as will be elaborated herein below.

In summary, another process of the invention comprises converting the compounds of formula Is, wherein X is —OR to the corresponding compounds of formula Is, wherein X is

The invention will be further described herein below.

FURTHER DESCRIPTION OF THE INVENTION AND PREFERRED EMBODIMENTS

The compounds of our invention can be represented by the following sub-generic formulas:

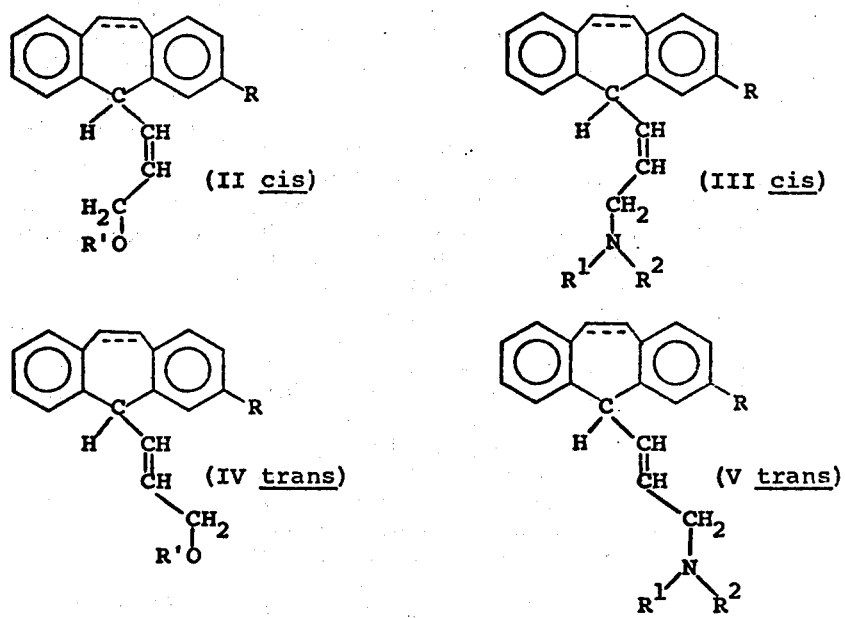

wherein the dotted line indicates either a saturated (ethylene) bridge or a double bond (vinyl) bridge between the C-10 and C-11 carbon atoms;

R is hydrogen, lower alkyl, lower alkoxy, lower alkenyl, halo, trifluoromethyl, alkylsulfonyl, trifluoromethylsulfonyl, thioalkyl, dialkylsulfamoyl, cyano;

R$^1$ and R$^2$ are independently hydrogen, lower alkyl, lower cycloalkyl, phenylalkyl, hydroxyalkoxyalkyl, phenacyl or substituted phenacyl; or R$^1$ and R$^2$ together with the nitrogen atom to which they are joined from a heterocyclic ring having from 5 through 7 ring atoms having from 1 or 2 hetero atoms selected from the group consisting of nitrogen, sulfur and oxygen, wherein one of said hetero atoms is the joining nitrogen atom, or R$^1$ and R$^2$ together with the nitrogen atom to which they are joined form a substituted heterocyclic ring having the formula:

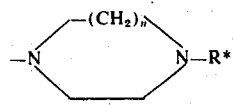

wherein n is 1 or 2 and R* is H, lower alkyl, or hydroxy (lower)alkyl; and

—OR' is hydroxy, acid labile ether or the group —O—SO$_2$R$_2$' wherein R$_2$' is lower alkyl.

Also encompassed within our invention are pharmaceutically acceptable salts of the compounds of formulas III and V.

Definitions

As used herein above and below, the following terms have the following meanings unless expressly stated to the contrary. The term lower alkyl refers to both straight and branched chain alkyl groups having a total of from 1 through 6 carbon atoms and thus includes primary, secondary and tertiary alkyl groups. Typical lower alkyls include, for example, methyl, ethyl, n-propyl, isopropyl, n-butyl, t-butyl, n-hexyl and the like. The term cycloalkyl refers to cyclic hydrocarbon groups having from 3 through 7 carbon atoms such as, for example, cyclopropyl, cyclopentyl, cycloheptyl, and the like. The term haloalkyl refers to such groups having from one through four carbon atoms and from one through four halo atoms. Typical haloalkyl groups include, for example, trifluoromethyl, 1,2,2,2-tetrachloroethyl and the like. The term lower alkenyl refers to monoethylenically unsaturated aliphatic groups having from 2 through 6 carbon atoms and wherein the double bond can be between any two adjacent carbon atoms. Typical lower alkenyl groups include, for example, vinyl, propenyl, and the like. The term alkoxy refers to the group having the formula R'O— wherein R' is lower alkyl. Typical alkoxy groups include, for example, methoxy, ethoxy, t-butoxy and the like. The term (lower alkoxy) lower alkyl refers to the group —R'—OR' wherein R' is lower alkyl and OR' is lower alkoxy. The term hydroxy lower alkyl refers to groups having the formula HOR' wherein R' is lower alkyl. Typical hydroxyalkyl groups include, for example, hydroxymethyl, α-hydroxyethyl, β-hydroxypropyl, hydroxyisopropyl, hydroxy-t-butyl and the like. The term hydroxyalkoxyalkyl refers to the group having the formula —R'—OR''—OH wherein R' and R'' are the same or different lower alkyls. Typical hydroxyalkoxyalkyl groups thus include, for example, hydroxymethoxymethyl, β-(β-hydroxyethyl)-ethyl and the like. The term acid labile ether refers to ether groups which can be removed by mild acid hydrolysis from the parent moiety to which they are attached and preferably having from 2 to 12 carbon atoms. Typical acid labile ether groups include, for example, methoxymethoxy; 1'-methoxyethoxy; 1'—ethoxyethoxy; phenoxymethoxy; 2'-methoxyprop-2'-oxy; tetrahydropyranyl-2'-oxy; tetrahydrofuran-2'-oxy; 2'-butoxyprop-2'-oxy; 1'-pent-1''-oxycyclohexyl-1'-oxy; and the like.

The term phenylalkyl refers to a phenyl substituted alkyl group such as benzyl, phenylethyl, o-, m-, or p-methylbenzyl, and the like, preferably having up to ten carbons. The term substituted phenyl refers to phenyl groups substituted at one or more of the ortho, meta or para positions with a hydroxy, lower alkyl, acyloxy, lower alkoxy, nitro or halo group. Typical substituted phenyl groups include, for example, p-hydroxyphenyl, p-tolyl, p-acetoxyphenyl, p-nitrophenyl, p-fluorophenyl, p-chlorophenyl and the corresponding ortho and meta isomers. The term substituted phenacyl refers to the group having the formula

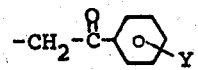

wherein Y is hydrogen, halo, halo alkyl having from one through four carbon atoms and from one through four halo atoms, lower alkyl, or lower alkoxy, and Y can be at any position on the phenyl rings.

The term lower alkylamino refers to the group having the formula R'HN— wherein R' is lower alkyl. The term dialkylamino refers to the group R'R''N— wherein R' and R'' are the same or different lower alkyls.

The term thioalkyl refers to groups having the formula R'S— wherein R' is lower alkyl. The term alkylsulfonyl refers to groups having the formula

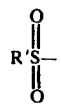

wherein R' is lower alkyl. The term sulfamoyl refers to the groups having the formula

The term alkylsulfamoyl refers to groups having the formula

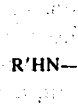

wherein R' is lower alkyl. The term dialkylsulfamoyl refers to groups having the formula

wherein R$_1$' and R$_2$' are lower alkyl. Typical dialkylsulfamoyls include, for example, dimethylsulfamoyl, N-isopropyl-N-methylsulfamoyl, N-ethyl-N-methylsulfamoyl and the like.

The term N-heterocycle refers to both saturated and unsaturated heterocycles having from five through seven ring atoms, one of which is nitrogen and which can optionally also contain a second hetero element ring atom selected from the group of nitrogen, sulfur and oxygen. Also, encompassed within the term are substituted N-heterocyclics having one or two substituents independently selected from the group of lower alkyl, hydroxylower alkyl, and halo. Typical N-heterocycles thus include, for example, those groups having the formulas:

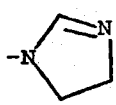 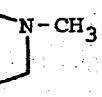 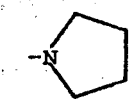

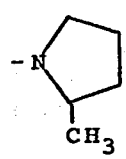  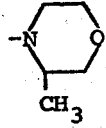

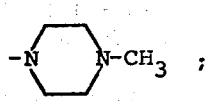 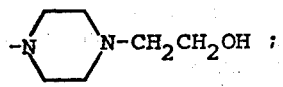 

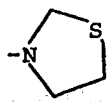  

and the like.

The term pharmaceutically acceptable salts refers to pharmaceutically acceptable acid addition salts which do not adversely affect the pharmaceutical properties of the parent compounds. With respect to the addition salts, suitable inorganic anions include, for example, chloride, bromide, iodide, sulfate, phosphate, nitrate, and the like. Suitable organic anions include, for example, lactate, picrate, tartrate, maleate, fumarate, citrate, succinate, toluenesulfonate, ascorbate, pamoate, nicotinate, adipate, glyconate and the like.

All temperatures and temperature ranges refer to the Centigrade scale and the term ambient or room temperature refers to about 20°C.

The abbreviation CNS refers to the central nervous system.

Typical illustrations of the compounds of formula III cis, of our invention, can be had, for example, by reference herein below to Examples 1 and 7.

With respect to the compounds of formula III cis, the preferred R substituents are hydrogen, chloro, cyano, trifluoromethyl and N,N-dimethylsulfamoyl.

With respect to the compounds of formula III cis, the preferred $R^1$ and $R^2$ substituents are those wherein one of $R^1$ or $R^2$ is methyl and the other is selected from the group consisting of hydrogen, methyl and p-chlorophenacyl or wherein $R^1$ and $R^2$ together with the nitrogen atom to which they are joined form a substituted heterocycle selected from the group consisting of N-(N'-methyl)piperazinyl and N-(N'-β-hydroxyethyl)-piperazinyl.

The particularly preferred compounds of formula III cis having a vinyl bridge between the C-10 and C-11 carbon atoms are:

5-(3-dimethylaminoprop-cis-1-enyl)-5H-dibenzo[a,d]cycloheptene;
5-(3-methylaminoprop-cis-1-enyl)-5H-dibenzo[a,d]cycloheptene;
5-(3-[N-methyl-N-(p-chlorophenacyl)]aminoprop-cis-1-enyl)-5H-dibenzo[a,d]cycloheptene;
5-(3-[N'-(β-hydroxyethyl)N-piperazino]prop-cis-1-enyl)-5H-dibenzo[a,d]cycloheptene;
3-cyano-5-(3-dimethylaminoprop-cis-1-enyl)-5H-dibenzo[a,d]cycloheptene;
5-(3-dimethylaminoprop-cis-1-enyl)-3-trifluoromethyl-5H-dibenzo[a,d]cycloheptene;
5-(3-dimethylaminoprop-cis-1-enyl)-3-dimethylsulfamoyl-5H-dibenzo[a,d]cycloheptene;
5-(3-[N'-(β-hydroxyethyl)N-piperazino]prop-cis-1-enyl)-3-trifluoromethyl-5H-dibenzo[a,d]cycloheptene;
3-cyano-5-(3-[N'-methyl-N-piperazino]prop-cis-1-enyl)-5H-dibenzo[a,d]cycloheptene;
3-chloro-5-(3-dimethylaminoprop-cis-1-enyl)-5H-dibenzo[a,d]cycloheptene;

and the corresponding pharmaceutically acceptable salts thereof.

The particularly preferred compounds of formula III cis having a saturated (ethylene) bridge between the C-10 and C-11 carbon atoms are:

10,11-dihydro-5-(3-dimethylaminoprop-cis-1-enyl)-5H-dibenzo[a,d]cycloheptene;
10,11-dihydro-5-(3-methylaminoprop-cis-1-enyl)-5H-dibenzo[a,d]cycloheptene;
10,11-dihydro-5-(3-[N-methyl-N-(p-chlorophenacyl)]aminoprop-cis-1-enyl)-5H-dibenzo[a,d]cycloheptene;
10,11-dihydro-5-(3-[N'-(β-hydroxyethyl)N-piperazino]prop-cis-1-enyl)-5H-dibenzo[a,d]cycloheptene;
3-cyano-10,11-dihydro-5-(3-dimethylaminoprop-cis-1-enyl)-5H-dibenzo[a,d]cycloheptene;
10,11-dihydro-5-(3-dimethylaminoprop-cis-1-enyl)-3-trifluoromethyl-5H-dibenzo[a,d]cycloheptene;
10,11-dihydro-5-(3-dimethylaminoprop-cis-1-enyl)-3-dimethylsulfamoyl-5H-dibenzo[a,d]cycloheptene;

10,11-dihydro-5-(3-[N'-(β-hydroxyethyl)N-piperazino]prop-cis-1enyl)-3-trifluoromethyl-5H-dibenzo[a,d]cycloheptene;

3-cyano-10,11-dihydro-5-(3-[N'-methyl-N-piperazino]prop-cis-1-enyl)-5H-dibenzo[a,d]cycloheptene;

3-chloro-10,11-dihydro-5-(3-dimethylaminoprop-cis-1-enyl)-5H-dibenzo[a,d]cycloheptene;

and the corresponding pharmaceutically acceptable salts thereof.

Typical illustrations of the compounds of formula V trans, of our invention, can be had, for example, by reference herein below to Examples 2 and 7.

With respect to the compounds of formula V trans, the preferred R substituents are hydrogen and chloro.

With respect to the compounds of formula V trans, the preferred $R^1$ and $R^2$ substituents are those wherein one of $R^1$ or $R^2$ is methyl and the other is selected from the group consisting of hydrogen, methyl and p-chlorophenacyl.

The particularly preferred compounds of formula V trans having a vinyl bridge between the C-10 and C-11 carbon atoms are:

5-(3-dimethylaminoprop-trans-1-enyl)-5H-dibenzo[a,d]cycloheptene;

5-(3-methylaminoprop-trans-1-enyl)-5H-dibenzo[a,d]cycloheptene;

5-(3-[N-methyl-N-(p-chlorphenacyl)]aminoprop-trans-1-enyl)-5H-dibenzo[a,d]cycloheptene;

3-chloro-5-(3-dimethylaminoprop-trans-1-enyl)-5H-dibenzo[a,d]cycloheptene;

and the corresponding pharmaceutically acceptable salts thereof.

The particularly preferred compounds of formula V trans having a saturated (ethylene) bridge between the C-10 and C-11 carbon atoms are:

10,11-dihydro-5-(3-dimethylaminoprop-trans-1-enyl)-5H-dibenzo[a,d]cycloheptene;

10,11-dihydro-5-(3-methylaminoprop-trans-1-enyl)-5H-dibenzo[a,d]cycloheptene;

10,11-dihydro-5-(3-[N-methyl-N-(p-chlorophenacyl)]aminoprop-trans-1-enyl)-5H-dibenzo[a,d]cycloheptene;

3-chloro-10,11-dihydro-5-(3-dimethylaminoprop-trans-1-enyl)-5H-dibenzo[a,d]cycloheptene;

and the corresponding pharmaceutically acceptable salts thereof.

Typical illustrations of the compounds of formulas II cis and IV trans can be had, for example, herein below by reference to Examples 3, 4, 5 and Examples 3A 4A, 5 and 6, respectively.

Since the primary utility of the compounds of formulas II cis and IV trans is as intermediates, the preferred R-substituents in the compounds of formulas II and IV are the same as those listed above for the preferred compounds of formulas III cis and V trans, respectively, and the particulary preferred compounds of formulas II cis and IV trans are the corresponding precursors (or intermediates) of the corresponding particularly preferred compounds of formulas III cis and V trans enumerated herein above.

Considering the particularly preferred compounds of formula III cis in terms of therapeutic CNS activity in greater detail, the following compounds and their pharmaceutically acceptable salts exhibit a significant and exceptional combination of anti-depressant and tranquilizing activities and can be classified as tranquilizing (or sedative) anti-depressants:

5-(3-dimethylaminoprop-cis-1-enyl)-5H-dibenzo[a,d]cycloheptene;

10,11-dihydro-5-(3-dimethylaminoprop-cis-1-enyl)-5H-dibenzo[a,d]cycloheptene;

3-chloro-5-(3-dimethylaminoprop-cis-1-enyl)-5H-dibenzo[a,d]cycloheptene;

3-chloro-10,11-dihydro-5-(3-dimethylaminoprop-cis-1-enyl)-5H-dibenzo[a,d]cycloheptene;

10,11-dihydro-5-(3-[N-methyl-N-(p-chlorophenacyl)]-aminoprop-cis-1-enyl)-5H-dibenzo[a,d]cycloheptene; and 5-(3-[N-methyl-N-(p-chlorophenacyl)]aminoprop-cis-1-enyl)-5H-dibenzo[a,d,]cycloheptene.

The pharmacological spectrum of these compounds is particularly notable in that, based on laboratory animal studies, they exhibit anti-depressant activity commmparable to that of imipramine and also exhibit a tranquilizing or sedative activity greater than meprobamate or phenobarbitol.

The following particularly preferred compounds of formula V trans and their pharmaceutically acceptable salts exhibit potent anti-depressant activity with minimal tranquilizing or sedative activity.

5-(3-methylaminoprop-trans-1-enyl)-5H-dibenzo[a,d]cycloheptene;

10,11-dihydro-5-(3-methylaminoprop-trans-1-enyl)-5H-dibenzo[a,d]cycloheptene;

5-(3-dimethylaminoprop-trans-1-enyl)-5H-dibenzo[a,d]cycloheptene; and 10,11-dihydro-5-(3-dimethylaminoprop-trans-1-enyl)-5H-dibenzo[a,d]cycloheptene.

The following particularly preferred compounds and their pharmaceutically acceptable salts exhibit potent tranquilizing or sedative activities with minimal anti-depressant activity:

3-cyano-10,11-dihydro-5-(3-dimethylaminoprop-cis-1-enyl)-5H-dibenzo[a,d]cycloheptene;

10,11-dihydro-5-(3-[N'-(β-hydroxyethyl)N-piperazino]prop-cis-1-enyl)-3-trifluoromethyl-5H-dibenzo[a,d]cycloheptene;

3-cyano-10,11-dihydro-5-(3-[N'-β-hydroxyethyl-N-piperazino]prop-cis-1-enyl)-5H-dibenzo[a,d]cycloheptene; and 5-(3-[N'-(β-hydroxyethyl)N-piperazino]prop-cis-1-enyl)-3-trifluoromethyl-5H-dibenzo[a,d]cycloheptene.

One process of our invention for preparing the compounds of formula III cis of our invention can be represented by the following schematic overall reaction equation:

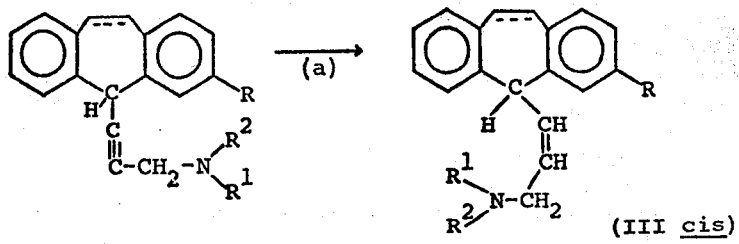

wherein R, R¹, R² and the dotted bond line have the same meaning as set forth herein above.

This reaction (step a) can be effected by hydrogenating the corresponding starting material of formula A, preferably in an inert organic solvent, in the presence of a suitable noble metal catalyst. Suitable noble metals include, for example, palladium, platinum, rhodium, iridium and the like or mixtures thereof.

catalyst:substrate ratio, we have found that good results are obtained by using an approximately equal portion by weight of catalyst to the substrate (i.e. starting material of formula A), however, both greater and smaller catalyst:substrate ratios can also be used.

The compounds of formula V trans can be prepared according to the invention by reduction of the corresponding compounds of formula A:

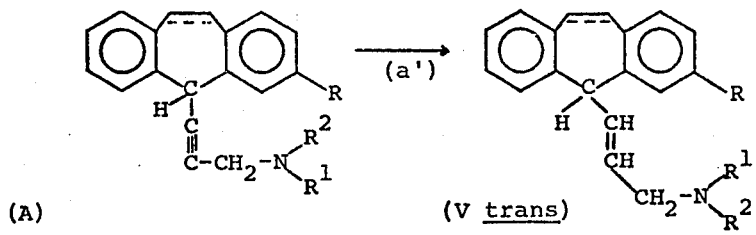

Preferably, the catalyst is a deactivated palladium catalyst of the Lindlar type (see Fieser and Fieser, *Reagents for Organic Synthesis*, p. 566, John Wiley and Sons, New York (1967), and Lindlar, Helv., v. 35, p. 446 (1952)), or the catalyst can be deactivated as it is used in the instant treatment by the addition of a small amount of aromatic amine (e.g. quinoline). The palladium catalyst can also be deactivated by using an amine solvent such as, for example, pyridine. Other suitable inert organic solvents which can be used include, for example, alcohols such as, for example, methanol, ethanol, and the like, ethers such as, for example, diethyl ether, and the like, and esters such as, for example, ethyl acetate and the like. Typically, this treatment is conducted at temperatures in the range of about from 0° C to the boiling point of the particular solvent being employed. Preferably, temperatures in the range of about from 20° to 60°C are used. Treatment times can vary over a wide range, depending on the weight ratio of catalyst to substrate, the inert solvent, the temperature, hydrogen pressure and the particular substrate being treated. Typically, treatment times are in the range of about from ½ to 18 hours. Progress of the hydrogenation can be conveniently monitored by thin-layer chromatographic examination of reation samples. Optimum conditions can then be determined by routine trial and error experimentation well within the scope of those skilled in the art. With respect to the wherein R, R¹, R² and the dotted bond line have the same meaning as set forth herein above.

This reaction can be conveniently effected by treating the compounds of formula A with an elemental alkali metal in anhydrous liquid ammonia. Typically this treatment is conducted at temperatures in the range of about from −78°C to the boiling point of anhydrous ammonia (i.e. −33°C), and preferably is conducted at about or just under the boiling point of the ammonia solvent. Optionally, the treatment can also be conducted in the presence of a suitable inert organic co-solvent such as, for example, tetrahydrofuran, ethylene glycol dimethyl ether, diethyl ether and the like. Accordingly, where a co-solvent is used, the treatment can be conducted at the boiling point of the ammonia co-solvent mixture. Typically, treatment times in the range of about from 5 to 60 minutes and preferably about 15 to 25 minutes are used. Also typically a mole ratio of about two or more gram atoms of alkali metal per mole of substrate (i.e. compound of formula A) is used. Suitable alkali metals which can be used include, for example, liithium, sodium and potassium The starting materials of formula A can be prepared according to the procedure described in U.S. Pat. No. 3,309,404, or can be prepared according to the following process, of the invention, which can be conveniently schematically represented by the following sequence of overall reaction equations:

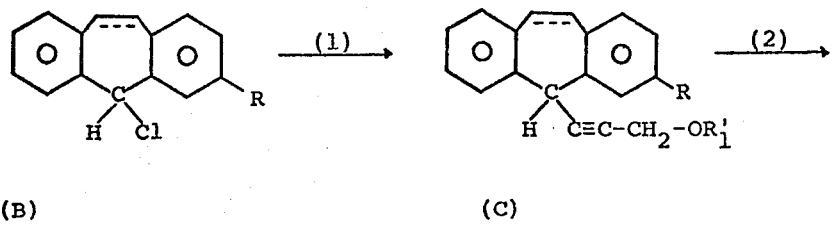

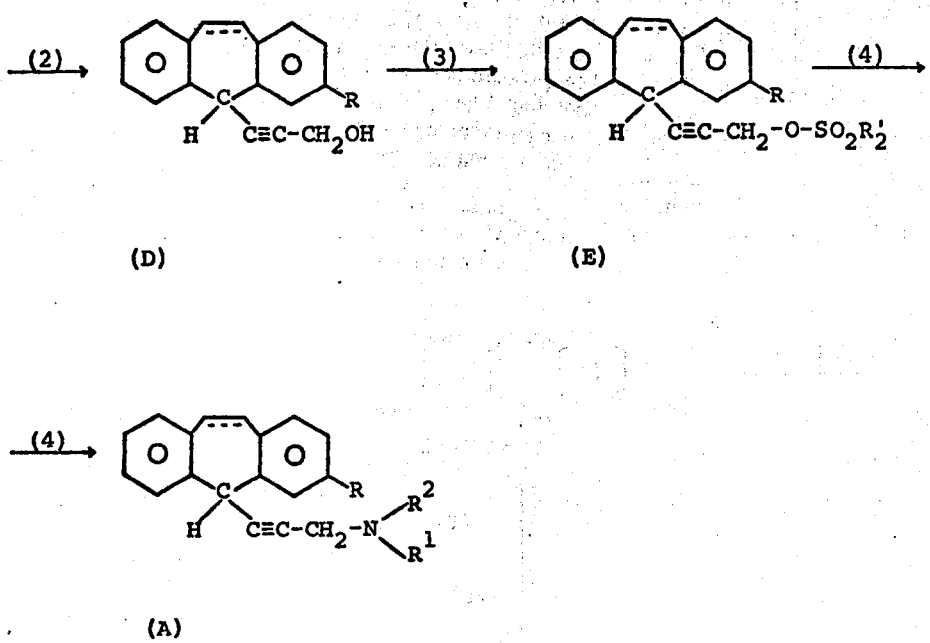

(D) (E)

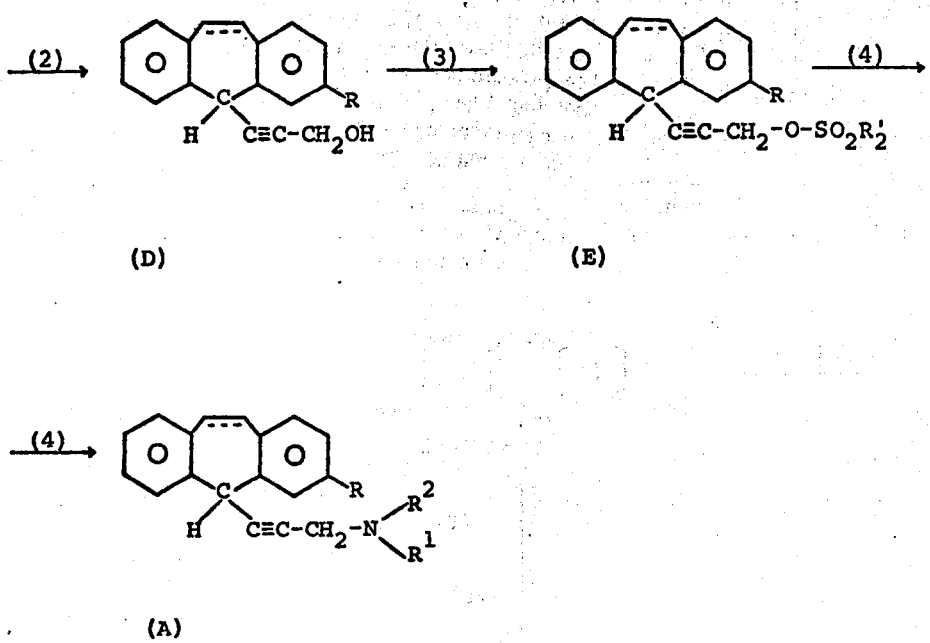

(A)

wherein $OR_1'$ is a labile ether; $R_2'$ is lower alkyl (preferably methyl); and R, $R^1$ and $R^2$ are as defined herein above.

Step 1 of the above process can be conveniently effected by treating the compound of formula B, in a suitable inert organic solvent, with a suitable propyne ether organo-metallic reagent. Typically, this treatment is conducted at temperatures in the range of about from 20° to 85°C, preferably about from 40° to 70°C, for about from ½ to 18 hours, and preferably about from 1 to 4 hours. Typically, a mole ratio in the range of about from 1 to 1.5 moles of organo-metallic reagent is used per mole of compound of formula B. Preferably, the treatment is conducted under anhydrous conditions and under an inert atmosphere (e.g. nitrogen). Suitable inert organic solvents which can be used include, for example, tetrahydrofuran, tetrahydropyran, and the like. Suitable propynyl ether organo-metallic reagents which can be used include those reagents which function in a similar manner as classic Grignard Reagents and include, for example, 3-(2-tetrahydropyranyloxy)-prop-1-ynyl-magnesium chloride;
3-(2-tetrahydropyranyloxy)-prop-1-ynyl-lithium;
3-(1-methoxycyclohexyloxy)-prop-1-ynyl-1-magnesium chloride;

and the like. The organo-metallic regents, used in the practice of the above process, can be prepared according to known procedures such as, for example, described by Edward et al, J. Med. Chem., vol. 14, 1190 (1971) and by Landor et al in J. Chem. Soc., page 185 (1967) or in Preparation 3, described herein below, or by obvious modifications of such procedures. The starting materials of formula B can be prepared according to known procedures such as, for example, described by G. Berti in Gazz. Chim. Ital., v. 87, 293-309 (1957), or according to the procedure described herein below in Preparation 2, or by obvious modifications of such procedures.

In step 2 of this process the ether moiety is cleaved by hydrolysis to yield the corresponding hydroxy substituent. This can be conveniently effected by treatment with an aqueous acid solution in an organic solvent according to conventional hydrolysis procedures. For example, typical hydrolysis conditions can be found by reference to Djerassi, Steroid Reactions, pages 76–79 (1963). Preferably the treatment is monitored by any suitable procedure, conveniently thin-layer chromatography, and the treatment continued until hydrolysis is indicated as substantially complete.

Step 3 of the above process can be conveniently effected by treating the compound of formula D with an alkyl sulfonyl chloride in an organic solvent containing a small quantity of an organic base, according to the procedure of R. K. Crossland and K. L. Servis, J. Org. Chem., 35, 3195 (1970).

Step 4 can be effected by treating the sulfonic ester intermediate of formula E, of the invention, with the appropriate amine

where $R^1$ and $R^2$ are as previous defined. For example, by treating the compounds of formula E with dimethylamine, the corresponding compounds of formula A wherein each of $R^1$ and $R^2$ is methyl are obtained. Similarly, treatment with a monoalkylamine will yield the corresponding compound of formula A wherein one of $R^1$ or $R^2$ is the corresponding alkyl group and the other is hydrogen. Correspondingly, using a heterocyclic amine such as, for example, piperidine; pyrrolidine; or morpholine will respectively yield the corresponding piperidinyl, pyrrolidinyl, and morpholino derivatives of formula A. Preferably the reaction is conducted in a suitable inert organic solvent. Further, although optimum conditions and solvents will vary according to the particular sulfonate ester of formula E and displacing amine used, the treatment is typically conducted at temperatures in the range of about from 0° to 70°C for about from ½ to 24 hours. However, temperatures and treatment times both above and below these ranges can also be used. Suitable inert organic solvents which can be used include, for example, methylene chloride, chloroform, methanol, diethyl ether and the like.

The compounds of formulas III cis and V trans, of the invention, can also be prepared according to another process of the invention via the intermediates of formulas II cis and IV trans. This process can be schematically represented by the following overall reaction equation sequence:

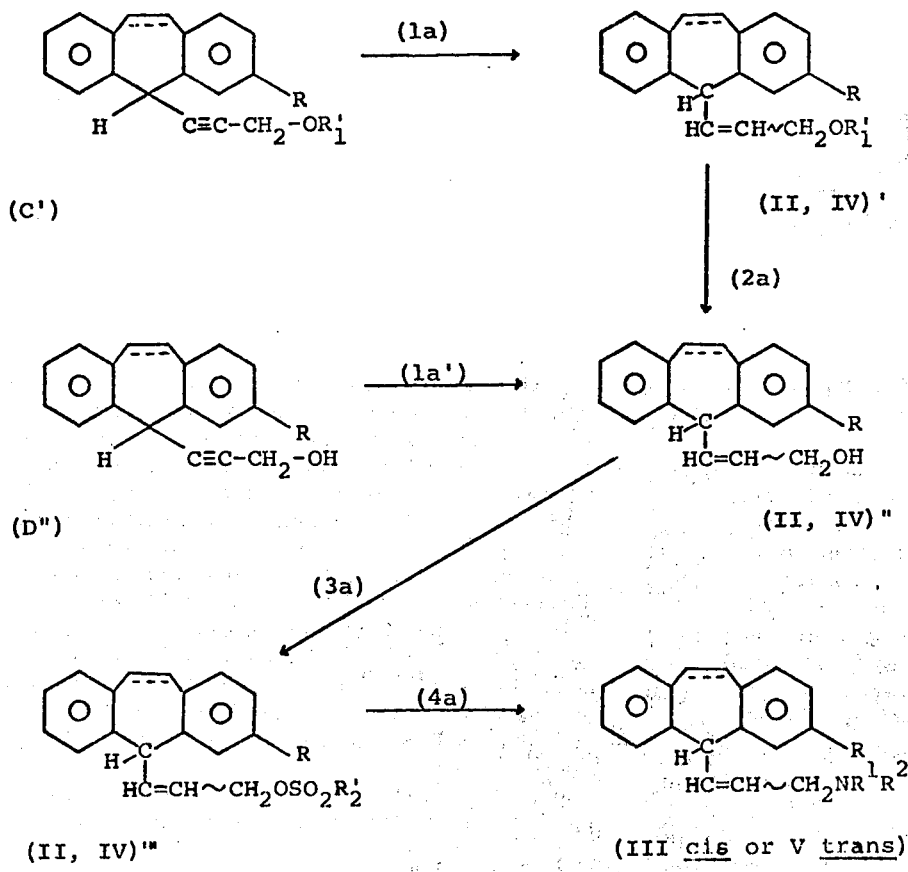

wherein R, $R^1$, $R^2$, $R_2'$ and $OR_1'$ are as defined herein above; and the wavy line (~) indicates either the cis isomer or the trans isomer depending on the particular treatment used in step 1a or step 1a'.

Steps 1a and 1a' can be effected by treating the corresponding starting material of formula C' or D'' according to the same respective procedures as described herein above with respect to the treatment of the starting material of formula A to yield the compounds of formula II cis or formula IV trans, depending on whether the cis or trans compound is desired.

Similarly, steps 2a, 3a and 4 can be effected according to the procedures described herein above with respect to steps 2, 3 and 4, respectively.

Unless otherwise indicated, it is preferable that the respective products of each step, in each process, are isolated prior to their subsequent use as starting materials for the next succeeding step. Separation and purification can be effected by suitable separation or purification procedures such as, for example, extraction, precipitation, filtration, washing, evaporation, crystallization, column and thin-layer chromatography, etc. Specific illustrations of typical separation and purification procedures can be had by reference to the corresponding Examples set forth herein below. However, other suitable separation and purification procedures could, of course, also be used.

The pharmaceutically acceptable salts, of the invention, can be conveniently prepared by treating the corresponding amine of formula III or V with an acid and can also to prepared by other conventional procedures such as, for example, ion exchange.

The compounds of formulas III cis and V trans and pharmaceutically acceptable salts thereof, of our invention, are useful in the treatment and/or pallitation of abnormal conditions, occurring in mammals, which are related to the central nervous system — e.g. depression-anxiety. In addition, the compounds and salts are also useful as antihistamines in the treatment of mammals. The compounds and salts can be administered either as solids or liquids. Typically, the compounds and salts are administered in combination with a pharmaceutical carrier in which the active component is dissolved, dispersed or suspended and can optionally contain small amounts of preservatives and/or pH-buffering agents. Suitable preservatives which can be used include, for example, benzyl alcohol and the like. Suitable buffering agents include, for example, sodium acetate and pharmaceutically acceptable phosphate salts and the like.

Suitable liquid compositions can, for example, take the form of solutions, emulsions, suspensions, syrups, elixirs, and the like. Similarly suitable solid compositions can be in the form of tablets, powders, capsules, pills, and the like, preferably in unit dosage form for simple administration or precise dosages. Suitable solid carriers which can be used include, for example, pharmaceutical grades of starch, lactose, sodium saccharin, talcum, and the like.

Where the compounds are being administered for the treatment or palliation of a central nervous system related disorder, the preferred dosage can vary over a wide range depending upon the particular subject and disorder, and severity of the disorder, being treated. Typically, the dosage range for such disorders will be in the range of about from 0.001 to 20 mg. per kg. of body weight, per day. Also, because of the problems incident to the treatment of central nervous system related disorders, close subject observation and control are desirable. Where the compounds are being applied as simple antihistamines, less stringent subject observation and control is generally needed and typically the lower dosage ranges, on the order of about from 0.001 to 5 mg. per kg. of body weight per day are used.

A further understanding of the invention can be had from the following non-limiting Preparations and Examples. Also, where needed, preparations and examples are repeated to provide sufficient starting materials for subsequent examples and preparations.

PREPARATION A

5H-Dibenzo[a,d]Cyclohepten-5-ol

In this preparation a solution containing 1.5 grams of sodium borohydride in 30 ml. of water containing 1.5 ml. of 3N aqueous sodium hydroxide is added to a solution containing 15.0 g. of dibenzo[a,d]cyclohepten-5-one in 200 ml. of methanol at room temperature, with stirring. The resulting mixture is stirred for 45 minutes and then an additional 0.5 g. of borohydride in 10 ml. of water is added and the mixture stirred at room temperatue for 60 hours. The reaction mixture is then cooled in an ice water bath while 300 ml. of water is slowly added with stirring. The resulting precipitate is collected by filtration and washed repeatedly with water and dried under vacuum affording a residue of 5H-dibenzo[a,d]cyclohepten-5-ol, which is sufficiently pure to use as starting material for subsequent preparations.

Similarly by following the same procedure as above but using the corresponding 5-one starting material, the following compounds are respectively prepared:

3-methyl-5H-dibenzo[a,d]cyclohepten-5-ol;
3-pentyl-5H-dibenzo[a,d]cyclohepten-5-ol;
3-ethenyl-5H-dibenzo[a,d]cyclohepten-5-ol;
3-fluoro-5H-dibenzo[a,d]cyclohepten-5-ol;
3-chloro-5H-dibenzo[a,d]cyclohepten-5-ol;
3-trifluoromethyl-5H-dibenzo[a,d]cyclohepten-5-ol;
3-methylmercapto-5H-dibenzo[a,d]cyclohepten-5-ol;
3-ethylsulfonyl-5H-dibenzo[a,d]cyclohepten-5-ol;
3-trifluoromethylsulfonyl-5H-dibenzo[a,d]cyclohepten-5-ol;
3-(N,N-dimethylsulfamoyl)-5H-dibenzo[a,d]cyclohepten-5-ol;
3-cyano-5H-dibenzo[a,d]cyclophepten-5-ol;
10,11-dihydro-5H-dibenzo[a,d]cyclophepten-5-ol;
10,11-dihydro-3-methyl-5H-dibenzo[a,d]cyclohepten-5-ol;
10,11-dihydro-3-pentyl-5H-dibenzo[a,d]cyclohepten-5-ol;
10,11-dihydro-3-methoxy-5H-dibenzo[a,d]cyclohepten-5-ol;
10,11-dihydro-3-ethenyl-5H-dibenzo[a,d]cyclohepten-5-ol;
10,11-dihydro-3-fluoro-5H-dibenzo[a,d]cyclohepten5ol;
3-chloro-10,11-dihydro-5H-dibenzo[a,d]cyclohepten-5-ol;
10,11-dihydro-3-trifluoromethyl-5H-dibenzo[a,d]cyclohepten-5-ol;
10,11-dihydro-3-methylmercapto-5H-dibenzo[a,d]cyclohepten-5-ol;
10,11-dihydro-3-ethylsulfonyl-5H-dibenzo[a,d]cyclohepten-5-ol;
10,11-dihydro-3-(N,N-dimethylsulfamoyl)-5H-dibenzo[a,d]cyclohepten-5-ol; and
3-cyano-10,11-dihydro-5H-dibenzo[a,d]cyclohepten-5-ol.

PREPARATION B

5-Chloro-5H-Dibenzo[a,d]Cycloheptene

In this preparation 25 ml. of thionyl chloride is added dropwise, with vigorous stirring, to a slurry of 5 g. of 5H-dibenzo[a,d]cyclohepten-5-ol in 50 ml. of anhydrous benzene containing five drops of pydridine, at about 0°C. The resulting mixture is continually stirred and allowed to heat to room temperature and then allowed to stand for 4 hours. The resulting mixture is then evaporated under vacuum to remove solvent and excess reagent affording a crystalline residue of 5-chloro-5H-dibenzo[a,d]cycloheptene which is then further dried under vacuum.

Similarly, by following the same procedure as above but respectively using the products of Preparation A as starting materials, the corresponding 5-chloro derivatives are respectively prepared.

PREPARATION C

5-(3-N,N-Dimethylaminoprop-1-ynyl)-5H-Dibenzo[a,d]Cycloheptene

In this preparation a solution of 3-dimethylaminoprop-1-ynyl magnesium chloride in 40 ml. of anhydrous tetrahydrofuran is prepared by the dropwise addition of 8.0 ml. of 1-N,N-dimethylamino-2-propyne to a stirred solution, under a nitrogen atmosphere, containing 0.046 moles of vinyl magnesium chloride in 40 ml. of anhydrous tetrahydrofuran. This mixture is heated at 50°C for 1 hour and then stirred at room temperature for an additional hour to ensure completion of the reaction. To this solution is added a solution containing 9.88 g. of 5-chloro-10,11-dihydro-5H-dibenzo[a,d]cycloheptene in 75 ml. of anydrous tetrahydrofuran, at room temperature. The resulting mixture is heated at reflux for two hours, then allowed to cool to room temperature and treated with an exccess of saturated aqueous ammonium chloride solution to decompose any excess 3-dimethylaminoprop-1-ynyl magnesium chloride. The mixture is then diluted with about ½ its volume of water and concentrated under vacuum to remove most of the tetrahydrofuran, and then extracted with ethyl ether. The ethereal extracts are combined and shaken several times with 1 Normal aqueous hydrochloric acid. The aqueous acid extracts are combined, then washed with ether and made slightly alkaline by the addition of dilute potassium hydroxide, and then extracted with three portions of ethyl ether. The ethereal extracts are combined and washed consecutively with water and saturated aqueous sodium chloride, and then dried over a mixture of anhydrous potassium carbonate and magnesium sulfate and evaporated under vacuum affording crud 5-(3-N,N-dimethylaminoprop-1-ynyl)-5H-dibenzo[a,d]cycloheptene, which is then divided into two approximately equal portions. The first portion is purified by a crystallization as the maleic acid salt via treatment with an ethereal solution of maleic acid.

The second portion of the crude product is further purified by column chromatography on silica gel employing hexaneaccetone for elution.

Similarly, by following the same procedure as above but respectively using the products of Preparation B as starting materials, the corresponding 5-(3-N,N-dimethylaminoprop-1-ynyl)- derivatives are respectively prepared.

PREPARATION D

This preparation illustrates methods of preparing ring substituted-ω-bromoacetophenones by bromination of the corresponding ring substituted acetophenone.

In this preparation a solution containing 1.76 g. (0.01 moles) of p-t-butylacetophenone in 20 ml. of chloroform is added to a briskly stirred suspension containing 4.47 g. (0.02 moles) of cupric bromide in 20 ml. of refluxing ethyl acetate. The resulting mixture is refluxed and stirred until the black suspended solid (cupric bromide) is observed to have disappeared. The mixture is then cooled to room temperature (i.e. about 20°C) and then filtered to remove precipitated cuprous bromide. The filtrate is treated with particulate activated charcoal and then filtered to remove the charcoal. The resulting filtrate is evaporated to dryness, under vacuum, affording a residue of p-t-butyl-ω-bromoacetophenone, which is sufficiently pure for use as starting material in the ensuing examples.

Similarly, by following the same procedure using the corresponding ring substituted acetophenones as starting materials, the following compounds are respectively prepared:

p-chloro-ω-bromoacetophenone;
o-chloro-ω-bromoacetophenone;
m-chloro-ω-bromoacetophenone;
p-fluoro-ω-bromoacetophenone;
o-fluoro-ω-bromoacetophenone;
m-fluoro-ω-bromoacetophenone;
p-bromo-ω-bromoacetophenone;
o-bromo-ω-bromoacetophenone;
m-bromo-ω-bromoacetophenone;
p-iodo-ω-bromoacetophenone;
o-iodo-ω-bromoacetophenone;
m-iodo-ω-bromoacetophenone;
p-methyl-ω-bromoacetophenone;
o-methyl-ω-bromoacetophenone;
m-methyl-ω-bromoacetophenone;
p-(t-butyl)-ω-bromoacetophenone;
o-(t-butyl)-ω-bromoacetophenone;
m-(t-butyl)-ω-bromoacetophenone;
p-(n-pentyl)-ω-bromoacetophenone;
o-(n-pentyl)-ω-bromoacetophenone;
m-(n-pentyl)-ω-bromoacetophenone;
p-trifluoromethyl-ω-bromoacetophenone;
o-trifluoromethyl-ω-bromoacetophenone;
m-trifluoromethyl-ω-bromoacetophenone;
p-(1,2,2,2-tetrachloroethyl)-ω-bromoacetophenone;
o-(1,2,2,2-tetrachloroethyl)-ω-bromoacetophenone;
m-(1,2,2,2-tetrachloroethyl)-ω-bromoacetophenone;
p-methoxy-ω-bromoacetophenone;
o-methoxy-ω-bromoacetophenone;
m-methoxy-ω-bromoacetophenone;
p-(t-butoxy)-ω-bromoacetophenone;
o-(t-butoxy)-ω-bromoacetophenone; and
m-(t-butoxy)-ω-bromoacetophenone.

PREPARATION 1

This preparation illustrates methods according to step 1 of the process for preparing the compounds of formula A. In this preparation a solution containing 8 g. of 5-chloro-5H-dibenzo[a,d]cycloheptene in 200 ml. of anhydrous tetrahydrofuran is added dropwise, under nitrogen, to a stirred solution containing 0.042 moles of 3-(2-tetrahydropyranyloxy)-prop-1-ynyl-1-magnesium chloride in 210 ml. of anhydrous tetrahydrofuran, at room temperature. The resulting mixture is heated for 2 hours at reflux and then allowed to stand, with stirring, for 16 hours at room temperature. The reaction mixture is then treated, first with 25 ml. of saturated aqueous ammonium chloride solution, then with 75 ml. of water, and then concentrated under reduced pressure to remove most of the organic solvent resulting in a two-phase liquid-liquid system, which is then shaken and extracted with three 60 ml. portions of ethyl ether. The ethereal extracts are combined and washed consecutively with 1N aqueous hydrochloric acid, saturated aqueous sodium bicarbonate and saturated brine. The washed extracts are dried over sodium sulfate-potassium carbonate and then evaporated under reduced pressure affording a residue of 5-[3-(2-tetrahydropyranyloxy)-prop-1-ynyl]-5H-dibenzo[a,d]cycloheptene, which is divided into two portions, one of which is further purified by column chromatography on silica gel. The other portion is used directly as starting material for the next step.

Similarly, by following the same procedure as above but respectively using the products of Preparation B as starting materials, the corresponding 5-[3-(2-tetrahydropyranyloxy)-prop-1-ynyl]- derivatives are respectively prepared.

Similarly, by following the same procedure as above but respectively using 3-(2-tetrahydrofuranyloxy)-prop-1-ynyl magnesium chloride and 3-(1-ethoxycyclohexyloxy)-prop-1-ynyl magnesium chloride in place of 3-(2-tetrahydropyranyloxy)-prop-1-ynyl-1 magnesium chloride, the corresponding 5-[3-(2-tetrahydrofuranyloxy)-prop-1-ynyl] and 5-[3-(1-ethoxycyclohexyloxy)-prop-1-ynyl] derivatives of the products of Preparation 2 are respectively prepared.

PREPARATION 2

This preparation illustrates methods according to step 2 of the process for preparing the compounds of formula A. In this preparation a solution containing 18.3 g. of crude 5-[3-(2-tetrahydropyranyloxy)-prop-1-ynyl]-5H-dibenzo[a,d]cycloheptene in 200 ml. of acetone and 20 ml. of concentrated hydrochloric acid is stirred at room temperature until thin-layer chromatographic analysis of a representative sample indicates hydrolysis to be complete (about 2 hours). The reaction mixture is neutralized by the addition of concentrated ammonium hydroxide and then evaporated under vacuum to remove acetone. The concentrated mixture is extracted with methylene chloride. The methylene chloride extract is washed consecutively with water and saturated brine, then dried over sodium sulfate. The dried extract is evaporated to dryness under vacuum affording a residue of crude 5-(3-hydroxyprop-1-ynyl)-5H-dibenzo[a,d]cycloheptene which is then further purified by column chromatography over silica gel, deactivated by the addition of 10%, by wt., of water, eluting with acetone-hexane mixtures.

Similarly, by following the same procedure as above but using the corresponding products of Preparation 1 as starting materials, the following products are respectively prepared:

5-(3-hydroxy-prop-1ynyl)-3-methyl-5H-dibenzo[a,d]cycloheptene;
5-(3-hydroxy-prop-1-ynyl)-3-pentyl-5H-dibenzo[a,d]cycloheptene;
5-(3-hydroxy-prop-1-ynyl)-3-methoxy-5H-dibenzo[a,d]cycloheptene;
5-(3-ethenyl-5-(3-hydroxy-prop-1-ynyl)-5H-dibenzo[a,d]cycloheptene;
3-fluoro-5-(3-hydroxy-prop-1-ynyl)-5H-dibenzo[a,d]cycloheptene;
3-chloro-5-(3-hydroxy-prop-1-ynyl)-5H-dibenzo[a,d]cycloheptene;
5-(3-hydroxy-prop-1-ynyl)-3-trifluoromethyl-5H-dibenzo[a,d]cycloheptene;
5-(3-hydroxy-prop-1-ynyl)-3-methylmercapto-5H-dibenzo[a,d]cycloheptene;
3-ethylsulfonyl-5-(3-hydroxy-prop-1-ynyl)-5H-dibenzo[a,d]cycloheptene;
5-(3-hydroxy-prop-1-ynyl)-3-trifluoromethylsulfonyl-5H-dibenzo[a,d]cycloheptene;
3-(N,N-dimethylsulfamoyl)-5-(3-hydroxy-prop-1-ynyl)-5H-dibenzo[a,d]cycloheptene;
3-cyano-5-(3-hydroxy-prop-1-ynyl)-5H-dibenzo[a,d]cycloheptene;
10,11-dihydro-5-(3-hydroxy-prop-1-ynyl)-5H-dibenzo[a,d]cycloheptene;
10,11-dihydro-5-(3-hydroxy-prop-1-ynyl)-3-methyl-5H-dibenzo[a,d]cycloheptene;
10,11-dihydro-5-(3-hydroxy-prop-1-ynyl)-3-pentyl-5H-dibenzo[a,d]cycloheptene;
10,11-dihydro-5-(3-hydroxy-prop-1-ynyl)-3-methoxy-5H-dibenzo[a,d]cycloheptene;
10,11-dihydro-3-ethenyl-5-(3-hydroxy-prop-1-ynyl)-5H-dibenzo[a,d]cycloheptene;
10,11-dihydro-3-fluoro-5-(3-hydroxy-prop-1-ynyl)-5H-dibenzo[a,d]cycloheptene;
3-chloro-10,11-dihydro-5-(3-hydroxy-prop-1-ynyl)-5H-dibenzo[a,d]cycloheptene;
10,11-dihydro-5-(3-hydroxy-prop-1-ynyl)-3-trifluoromethyl-5H-dibenzo[a,d]cycloheptene;
10,11-dihydro-5-(3-hydroxy-prop-1-ynyl)-3-methylmercapto-5H-dibenzo[a,d]cycloheptene;
10,11-dihydro-3-ethylsulfonyl-5-(3-hydroxy-prop-1-ynyl)-5H-dibenzo[a,d]cycloheptene; and
10,11-dihydro-3-N,N-dimethylsulfamoyl-5-(3-hydroxy-prop-1-ynyl)-5H-dibenzo[a,d]cycloheptene.

PREPARATION 3

This preparation illustrates methods according to step 3 of the process for preparing the compounds of formula A. In this preparation a solution containing 0.25 g. of 5-(3-hydroxy-prop-1-ynyl)-5H-dibenzo[a,d]cycloheptene in 25 ml. of anhydrous methylene chloride containing 0.25 ml. of triethylamine is stirred and cooled to maintain the temperature between 0°C and −10°C and 0.15 ml. of methanesulfonyl chloride is added. Cooling is then discontinued and the temperature of the mixture allowed to rise, with stirring, for 15 minutes. The solution is then poured into ice water, resulting in a two-phase organic-aqueous mixture. The organic layer is separated and washed successively with ice cold 1 Normal aqueous hydrochloric acid, water, and saturated brine, and then dried over sodium sulfate and evaporated under vacuum yielding 5-(3-methanesulfonyloxyprop-1-ynyl)-5H-dibenzo[a,d]cycloheptene which is of sufficient purity to be used directly as starting material for subsequent examples.

Similarly, by following the same procedure as above but respectively using the corresponding products of Preparation 2 as starting materials, the corresponding 5-(3-methanesulfonyloxyprop-1-ynyl) derivatives are respectively prepared.

PREPARATION 4

This preparation illustrates the fourth and final step of the process for preparing the compounds of formula A. In this preparation 1 ml. of 40% (wt.) aqueous methylamine, and a sufficient amount of sodium sulfate to absorb the aqueous layer from the reaction mixture (i.e. about 5 g.) is added to a solution containing 0.30 g. of 5-(3-methanesulfonyloxyprop-1-ynyl)-5H-dibenzo[a,d]cycloheptene, prepared according to Preparation 3, in 35 ml. of methylene chloride at 20°C. The resulting mixture is stirred for 16 hours at room temperature and then filtered. The filtrate is recovered and evaporated under reduced pressure affording a residue which is dissolved in dilute aqueous hydrochloric acid (pH 1) and washed with ethyl ether.

The ether washes are further extracted with 2N aqueous hydrochloric acid, then the combined aqueous phases are made slightly alkaline by the addition of concentrated ammonium hydroxide and extracted with ethyl ether. The ethereal extracts are combined, washed successively with water and saturated brine and dried over sodium sulfate. The dried extracts are evaporated under reduced pressure affording 5-(3-N-methylaminoprop-1-ynyl)-5H-dibenzo[a,d] cycloheptene. A portion of this product is then further purified and recovered as the crystalline maleic acid salt by dissolution in ethyl ether and treatment with an ethereal solution of maleic acid.

Similarly, by following the same procedure as above but respectively using the corresponding 3-substituted-5-(3-methanesulfonyloxyprop-1-ynyl)-5H-dibenzo[a,d]cycloheptene and 10,11-dihydro analogs, the following compounds are respectively prepared:

3-methyl-5-(3-N-methylaminoprop-1-ynyl)-5H-dibenzo[a,d] cycloheptene;
5-(3-N-methylaminoprop-1-ynyl)-3-pentyl-5H-dibenzo[a,d] cycloheptene;
3-methoxy-5-(3-N-methylaminoprop-1-ynyl)-5H-dibenzo[a,d] cycloheptene;
3-ethenyl-5-(3-N-methylaminoprop-1-ynyl)-5H-dibenzo[a,d] cycloheptene;
3-fluoro-5-(3-N-methylaminoprop-1-ynyl)-5H-dibenzo[a,d] cycloheptene;
3-chloro-5-(3-N-methylaminoprop-1-ynyl)-5H-dibenzo[a,d] cycloheptene;
5-(3-N-methylaminoprop-1-ynyl)-3-trifluoromethyl-5H-dibenzo[a,d]cycloheptene;

5-(3-N-methylaminoprop-1-ynyl)-3-methylmercap-
to-5H-dibenzo[a,d]cycloheptene;
3-ethylsulfonyl-5-(3-N-methylaminoprop-1-ynyl)-
5H-dibenzo[a,d]cycloheptene;
5-(3-N-methylaminoprop-1-ynyl)-3-trifluoromethyl-
sulfonyl-5H-dibenzo[a,d]cycloheptene;
3-(N,N-dimethylsulfamoyl)-5-(3-N-methylamino-
prop-1-ynyl)-5H-dibenzo[a,d]cycloheptene;
3-cyano-5-(3-N-methylaminoprop-1-ynyl)-5H-
dibenzo[a,d] cycloheptene;
10,11-dihydro-5-(3-N-methylaminoprop-1-ynyl)-
5H-dibenzo [a,d]cycloheptene;
10,11-dihydro-3-methyl-5-(3-N-methylaminoprop-1-
ynyl)-5H-dibenzo[a,d]cycloheptene;
10,11-dihydro-5-(3-N-methylaminoprop-1-ynyl)-3-
pentyl-5H-dibenzo[a,d]cycloheptene;
10,11-dihydro-3-methoxy-5-(3-N-methylaminoprop-
1-ynyl)-5H-dibenzo[a,d]cycloheptene;
10,11-dihydro-3-ethenyl-5-(3-N-methylaminoprop-
1-ynyl)-5H-dibenzo[a,d]cycloheptene;
10,11-dihydro-3-fluoro-5-(3-N-methylaminoprop-1-
ynyl)-5H-dibenzo[a,d]cycloheptene;
3-chloro-10,11-dihydro-5-(3-N-methylaminoprop-1-
ynyl)-5H-dibenzo[a,d]cycloheptene;
10,11-dihydro-5-(3-N-methylaminoprop-1-ynyl)-3-
trifluoromethyl-5H-dibenzo[a,d]cycloheptene;
10,11-dihydro-5-(3-N-methylaminoprop-1-ynyl)-3-
methylmercapto-5H-dibenzo[a,d]cycloheptene;
10,11-dihydro-3-ethylsulfonyl-5-(3-N-methylamino-
prop-1-ynyl)-5H-dibenzo[a,d]cycloheptene;
10,11-dihydro-5-(3-N-methylaminoprop-1-ynyl)-3-
trifluoromethylsulfonyl-5H-dibenzo[a,d]cyclohep-
tene;
10,11-dihydro-3-(N,N-dimethylsulfamoyl)-5-(3-N-
methylaminoprop-1-ynyl)-5H-dibenzo[a,d]cy-
cloheptene; and
3-cyano-10,11-dihydro-5-(3-N-methylaminoprop-1-
ynyl)-5H-dibenzo[a,d]cycloheptene.

Similarly, by following the same procedure as above but respectively using dimethylamine and diethylamine in place of methylamine, the corresponding 5-(3-N,N-dimethylaminoprop-1-ynyl)- and 5-(3-N,N-diethylaminoprop-1-ynyl)- homologues of each of the above products are respectively prepared.

PREPARATION 5

This preparation illustrates methods of preparing cyclic amine derivatives of formula A. In this preparation 1 gram of N-β-hydroxyethyl-piperazine is added to a solution containing 0.31 g. of 5-(3-methanesulfonyl-prop-1-ynyl)-5H-dibenzo[a,d]cycloheptene, according to Example 3, in 20 ml. of dichloromethane at 0°C. The resulting mixture is monitored by thin-layer chromatographic analysis and allowed to stand at room temperature until conversion of the sulfonate ester is essentially complete. The mixture is then worked up and purified according to the procedure described in Example 4, yielding 5-[3-(N'-β-hydroxyethyl-1-piperazinyl)prop-1-ynyl]-5H-dibenzo[a,d]cycloheptene.

Similarly, by following the same procedure as above but respectively using the corresponding dibenzocycloheptene starting materials, the corresponding 5-[3-N'-β-hydroxyethyl-1-piperazinyl)prop-1-ynyl]analogs of the products enumerated in Preparation 4 are respectively prepared.

Similarly, by following the same procedure as above but respectively using piperidine, morpholine, pyrrolidine, and N-methylpiperazine in place of N-β-hydroxyethylpiperazine, the corresponding 5-[3-(N-piperidino)prop-1-ynyl]; 5-(3-[N-morpholino]prop-1-ynyl); 5-(3-[N-pyrrolidino]prop-1-ynyl); and 5-(3-[N'-methylpiperazino]prop-1-ynyl) analogs of each of the above products are respectively prepared.

PREPARATION 6

This preparation illustrates methods of preparing the side-chain phenacylamino derivatives of formula A. In this preparation 0.192 moles of 5-(3-N-methylamino-prop-1-ynyl)-5H-dibenzo[a,d]cycloheptene and 0.256 moles of p-chloro-ω-bromoacetophenone is dissolved in 1 ml. of benzene at 20°C. One milliliter of water containing 2 mg. of sodium sulfite and 20 mg. of sodium bicarbonate is then added with constant stirring. The mixture is then aged for 2 hours with constant stirring at 20°C and then poured into 20 ml. of a 1:2 (by vol.) mixture of water and ethyl ether resulting in a liquid-liquid two phase mixture. The ether phase is separated with water and dried over magnesium sulfate. The residue is then further purified by thin-layer chromatography on silica gel, employing a 10% acetone-90% benzene (by vol.) elution system, affording pure 5-(3-[N-methyl-N-(p-chlorophenacyl)] amino-prop-1-ynyl)-5H-dibenzo[a,d]cycloheptene.

Similarly, by following the same procedure as above but using the various 5-methylamino derivative products in Preparation 4 as starting materials, the corresponding phenacyl derivates are respectively prepared.

Similarly, by following the same procedure as above but replacing ω-bromoacetophenone with the various ω-haloacetophenone derivatives, prepared according to Preparation D, the corresponding substituted phenacyl analogs of each of the above products are respectively prepared.

EXAMPLE 1

This example illustrates methods of preparing the compounds of formula III cis of the invention. In this example a solution of 0.20 g. of 5-(3-N,N-dimethylaminoprop-1-ynyl)- 5H-dibenzo[a,d]cycloheptene in 10 ml. of pyridine is stirred with 0.05 g. of a 5%, wt., palladium on barium sulfate catalyst at ambient temperature in an atmosphere of hydrogen for 2 ½ hours. The reaction mixture is then filtered through diatomaceous earth. The diatomaceous filter is washed with 30 ml. of diethyl ether. The combined filtrates and washes are then washed consecutively with six 10 ml. portions of water, then with saturated aqueous sodium chloride solution, and then dried over magnesium sulfate and evaporated to dryness under vacuum. The resulting residue is subjected to a stream of nitrogen to remove any traces of pyridine, affording a residue of crude 5-(3-dimethylaminoprop-cis-1-enyl)-5H-dibenzo[a,d-]cycloheptene which is then further purified by preparative chromatography on silica gel employing a 90% chloroform-10% methanol (vol.) mixture as the developing solvent.

Similarly, by following the same procedure as above but respectively using the corresponding products of Preparation C, the following compounds are respectively prepared:

3-methyl-5-(3-N,N-dimethylaminoprop-cis-1-enyl)-
5H-dibenzo[a,d]cycloheptene;
5-(3-N,N-dimethylaminoprop-cis-1-enyl)-3-pentyl-
5H-dibenzo[a,d]cycloheptene;
3-methoxy-5-(3-N,N-dimethylaminoprop-cis-1-
enyl)-5H-dibenzo[a,d]cycloheptene;

3-ethenyl-5-(3-N,N-dimethylaminoprop-cis-1-enyl)-
  5H-dibenzo[a,d]cycloheptene;
3-fluoro-5-(3-N,N-dimethylaminoprop-cis-1-enyl)-
  5H-dibenzo[a,d]cycloheptene;
3-chloro-5-(3-N,N-dimethylaminoprop-cis-1-enyl)-
  5H-dibenzo[a,d]cycloheptene;
5-(3-N,N-dimethylaminoprop-cis-1-enyl)-3-tri-
  fluoromethyl-5H-dibenzo[a,d]cycloheptene;
5-(3-N,N-dimethylaminoprop-cis-1-enyl)-3-methyl-
  mercapto-5H-dibenzo[a,d]cycloheptene;
3-ethylsulfonyl-5-(3-N,N-dimethylaminoprop-cis-1-
  enyl)-5H-dibenzo[a,d]cycloheptene;
5-(3-N,N-dimethylaminoprop-cis-1-enyl)-3-tri-
  fluoromethylsulfonyl-5H-dibenzo[a,d]cyclohep-
  tene;
3-(N,N-dimethylsulfamoyl)-5-(3-N,N-dime-
  thylaminoprop-cis-1-enyl)-5H-dibenzo[a,d]cy-
  cloheptene;
3-cyano-5-(3-N,N-dimethylaminoprop-cis-1-enyl)-
  5H-dibenzo[a,d]cycloheptene;
10,11-dihydro-5-(3-N,N-dimethylaminoprop-cis-1-
  enyl)-5H-dibenzo[a,d]cycloheptene;
10,11-dihydro-3-methyl-5-(3-N,N-dimethylamino-
  prop-cis-1-enyl)-5H-dibenzo[a,d]cycloheptene;
10,11-dihydro-5-(3-N,N-dimethylaminoprop-cis-1-
  enyl)-3-pentyl-5H-dibenzo[a,d]cycloheptene;
10,11-dihydro-3-methoxy-5-(3-N,N-dimethylamino-
  prop-cis-1-enyl)-5H-dibenzo[a,d]cycloheptene;
10,11-dihydro-3-ethenyl-5-(3-N,N-dimethylamino-
  prop-cis-1-enyl)-5H-dibenzo[a,d]cycloheptene;
10,11-dihydro-3-fluoro-5-(3-N,N-dimethylamino-
  prop-cis-1-enyl)-5H-dibenzo[a,d]cycloheptene;
3-chloro-10,11-dihydro-5-(3-N,N-dimethylamino-
  prop-cis-1-enyl)-5H-dibenzo[a,d]cycloheptene;
10,11-dihydro-5-(3-N,N-dimethylaminoprop-cis-1-
  enyl)-3-trifluoromethyl-5H-dibenzo[a,d]cyclohep-
  tene;
10,11-dihydro-5-(3-N,N-dimethylaminoprop-cis-1-
  enyl)-3-methylmercapto-5H-dibenzo[a,d]cy-
  cloheptene;
10,11-dihydro-3-ethylsulfonyl-5-(3-N,N-dime-
  thylamino-prop-cis-1-enyl)-5H-dibenzo[a,d]cy-
  cloheptene;
10,11-dihydro-5-(3-N,N-dimethylaminoprop-cis-1-
  enyl)-3-trifluoromethylsulfonyl-5H-dibenzo[a,d-
  ]cycloheptene;
10,11-dihydro-3-(N,N-dimethylsulfamoyl)-5-(3-
  N,N-dimethylaminoprop-cis-1-enyl)-5H-diben-
  zo[a,d]cycloheptene; and
3-cyano-10,11-dihydro-5-(3-N,N-dimethylamino-
  prop-cis-1-enyl)-5H-dibenzo[a,d]cycloheptene.

Similarly, by following the same procedure, the products of Preparation 4–6 are respectively reduced to the corresponding compounds of formula III cis.

EXAMPLE 2

This example illustrates methods of preparing compounds of formula V trans of the invention. In this example a stirred solution containing 0.391 g. of the maleic acid salt of 10,11-dihydro-5-(3-N,N-dimethylaminoprop-1-ynyl)-5H-dibenzo[a,d]cycloheptene, prepared according to Preparation C, in a mixture of anhydrous liquid ammonia (redistilled from sodium) and 25 ml. of anhydrous tetrahydrofuran is treated with 0.42 g. metallic lithium at about −33°C. After 10 minutes, a color change is noted in the solution, indicating that the reaction has gone to completion. The reaction is quenched immediately by the addition of excess solid ammonium chloride. The anhydrous ammonia is then allowed to evaporate from the mixture resulting in a white slurry. The slurry is diluted with water and saturated aqueous sodium bicarbonate solution and then extracted twice with diethyl ether. The ethereal extracts are washed with several portions of saturated aqueous sodium chloride solution, dried over a mixture of magnesium sulfate and potassium carbonate, and evaporated to dryness under reduced pressure, resulting in a residue of crude 10,11-dihydro-5-(3-N,N-dimethylaminoprop-trans-1-enyl)-5H-dibenzo[a,d]cycloheptene which is then further purified by preparative layer chromatography over silica gel employing a 90% chloroform–10% methanol (vol.) mixture as the developing solvent. A portion of the purified product is added to a diethyl ether solution of hydrogen chloride resulting in precipitation of the hydrochloride salt of 10,11-dihydro-5-(3-N,N-dimethylaminoprop-trans-1-enyl)-5H-dibenzo[a,d]cycloheptene, which is then recovered by filtration and further purified by recrystallization from acetone-hexane.

Similarly, by following the same procedures as above but respectively using the corresponding products of Preparation C, as starting materials, the following compounds, and their corresponding hydrochloride salts are respectively prepared:

3-methyl-5-(3-N,N-dimethylaminoprop-trans-1-
  enyl)-5H-dibenzo[a,d]cycloheptene;
5-(3-N,N-dimethylaminoprop-trans-1-enyl)-3-pen-
  tyl-5H-dibenzo[a,d]cycloheptene;
3-methoxy-5-(3-N,N-dimethylaminoprop-trans-1-
  enyl)-5H-dibenzo[a,d]cycloheptene;
3-ethenyl-5-(3-N,N-dimethylaminoprop-trans-1-
  enyl)-5H-dibenzo[a,d]cycloheptene;
3-fluoro-5-(3-N,N-dimethylaminoprop-trans-1-
  enyl)-5H-dibenzo[a,d]cycloheptene;
3-chloro-5-(3-N,N-dimethylaminoprop-trans-1-
  enyl)-5H-dibenzo[a,d]cycloheptene;
5-(3-N,N-dimethylaminoprop-trans-1-enyl)-3-tri-
  fluoromethyl-5H-dibenzo[a,d]cycloheptene;
5-(3-N,N-dimethylaminoprop-trans-1-enyl)-3-
  methylmercapto-5H-dibenzo[a,d]cycloheptene;
3-ethylsulfonyl-5-(3-N,N-dimethylaminoprop-trans-
  1-enyl)-5H-dibenzo[a,d]cycloheptene;
5-(3-N,N-dimethylaminoprop-trans-1-enyl)-3-tri-
  fluoromethylsulfonyl-5H-dibenzo[a,d]cyclohep-
  tene;
3-(N,N-dimethylsulfamoyl)-5-(3-N,N-dime-
  thylaminoprop-trans-1-enyl)-5H-dibenzo[a,d]cy-
  cloheptene;
3-cyano-5-(3-N,N-dimethylaminopro-trans-1-enyl)-
  5-dibenzo[a,d]cycloheptene;
10,11-dihydro-5-(3-N,N-dimethylaminoprop-trans-
  1-enyl)-5H-dibenzo[a,d]cycloheptene;
10,11-dihydro-3-methyl-5-(3-N,N-dimethylamino-
  prop-trans-1-enyl)-5H-dibenzo[a,d]cycloheptene;
10,11-dihydro-5-(3-N,N-dimethylaminoprop-trans-
  1-enyl)-3-pentyl-5H-dibenzo[a,d]cycloheptene;
10,11-dihydro-3-methoxy-5-(3-N,N-dimethylamino-
  prop-trans-1-enyl)-5-dibenzo[a,d]cycloheptene;
10,11-dihydro-3-ethenyl-5-(3-N,N-dimethylamino-
  prop-trans-1-enyl)-5-dibenzo[a,d]cycloheptene;
10,11-dihydro-3-fluoro-5-(3-N,N-dimethylamino-
  prop-trans-1-enyl)-5H-dibenzo[a,d]cycloheptene;
3-chloro-10,11-dihydro-5-(3-N,N-dimethylamino-
  prop-trans-1-enyl)-5H-dibenzo[a,d]cycloheptene;

10,11-dihydro-5-(3-N,N-dimethylaminoprop-trans-1-enyl)-3-trifluoromethyl-5H-dibenzo[a,d]cycloheptene;

10,11-dihydro-5-(3-N,N-dimethylaminoprop-trans-1-enyl)-3-methylmercapto-5H-dibenzo[a,d]cycloheptene;

10,11-dihydro-3-ethylsulfonyl-5-(3-N,N-dimethylaminoprop-trans-1-enyl)-5H-dibenzo[a,d]cycloheptene;

10,11-dihydro-5-(3-N,N-dimethylaminoprop-trans-1-enyl)-3-trifluoromethylsulfonyl-5H-dibenzo[a,d]cycloheptene;

10,11-dihydro-3-(N,N-dimethylsulfamoyl)-5-(3-N,N-dimethylaminoprop-trans-1-enyl)-5H-dibenzo[a,d]cycloheptene; and 3-cyano-10,11-dihydro-5-(3-N,N-dimethylaminoprop-trans-1-enyl)-5H-dibenzo[a,d]cycloheptene.

Similarly, by following the same procedure, the products of the Preparations 4–6 are resspectively reduced to the corresponding compounds of formula V trans and a portion of ecah compound converted to the corresponding hydrochloride salt.

EXAMPLE 3

This example illustrates methods according to step 1a of my process for preparing the ethers of formula II cis of the invention. In this example a solution of 1.0 g. of 10,11-dihydro-5-(3-N-[2-tetrahydropyranyloxy)-prop-1-ynyl]-5H-dibenzo[a,d]cycloheptene in 30 ml. of ethyl acetate is stirred with 1.0 g. of Lindlar catalyst (see Fieser and Fieser, *Reagents for Organic Synthesis*, p. 566, John Wiley and Sons, New York (1967)), at 50°C under hydrogen at atmospheric pressure. Samples of the reaction mixture are periodically taken and examined by thin-layer chromatography to ascertain whether the reaction has gone to completion. After the reaction has gone to completion (about 3 hours), the stirring is discontinued and the catalyst is separated by filtration of the reaction mixture through diatomaceous earth. The filtrate is evaporated to dryness under reduced pressure affording an oily residue of 10,11-dihydro-5-[3-(2-tetrahydropyranyloxy)-prop-cis-1-enyl]-5H-dibenzo[a,d]cycloheptene which is sufficient purity for subsequent use.

Similarly, by following the same procedure, the products of Preparation 1 are respectively reduced to the corresponding ethers of formula II cis.

EXAMPLE 3A

This example illustrates methods according to step 1a of my process for preparing the ethers of formula IV trans, of the invention. In this example 0.14 g. of metallic sodium is added to a stirred solution of 0.70 g. of 10,11-dihydro-5-[3-(2-tetrahydropyanyloxy)-prop-1-ynyl]-5H-dibenzo [a,d]cycloheptene in a mixture of 50 ml. of anhydrous liquid ammonia (redistilled from sodium) and 25 ml. of dry tetrahydrofuran at about −33°C. After twenty minutes the reaction mixture changes color and is then quenched with the addition of excess solid ammonium chloride. The liquid ammonia is evaporated from the reaction mixture and the reaction mixture is then diluted with 50 ml. of diethyl ether and washed several times with saturated aqueous sodium chloride solution, resulting in the formation of a two phase liquid-liquid mixture. The diethyl ether layer is separated and dried over a mixture of magnesium sulfate and potassium carbonate and then evaporated to dryness under reduced pressure affording an oily residue of crude 10,11-dihydro-5-[3-(2-tetrahydropyranyloxy)-prop-trans-1-enyl]-5H-dibenzo[a,d]cycloheptene which is then further purified by preparative thin-layer chromatography over silica gel employing a 20% acetone-80% hexane (vol.) mixture as the developing solvent.

Similarly, by following the same procedure as above, the products of Preparation 1 are respectively reduced to the corresponding ethers of formula IV trans.

EXAMPLE 4

This example illustrates methods of preparing compounds of formula II cis of the invention. In this example a slurry of 0.32 g. of Lindlar catalyst in 25 ml. of ethanol is prereduced by stirring under an atmosphere of hydrogen for 2 hours at ambient temperature. To the slurry is then added 0.32 g. of 5-(3-hydroxy-prop-1-ynyl)-5H-dibenzo[a,d]cycloheptene and the resulting mixture stirred at room temperature in a hydrogen atmosphere for 1½ hours. Stirring is discontinued and the catalyst removed by filtration through a diatomaceous earth filter. The filtrate is recovered and evaporated to dryness under reduced pressure affording a crude residue of 5-(3-hydroxy-prop-cis-1-enyl)-5H-dibenzo[a,d]cycloheptene which is then further purified by preparative thin-layer chromatography over silica gel employing an 80% hexane-20% acetone (vol.) mixture as the developing solvent.

Similarly, by following the same procedure but using the corresponding products of Preparation 2 as starting materials, the following compounds are respectively prepared:

5-(3-hydroxy-prop-cis-1-enyl)-3-methyl-5H-dibenzo[a,d]cycloheptene;

5-(3-hydroxy-prop-cis-1-enyl)-3-pentyl-5H-dibenzo[a,d]cycloheptene;

5-(3-hydroxy-prop-cis-1-enyl)-3-methoxy-5H-dibenzo[a,d]cycloheptene;

5-(3-ethenyl-5-(3-hydroxy-prop-cis-1-enyl)-5H-dibenzo[a,d]cycloheptene;

3-fluoro-5-(3-hydroxy-prop-cis-1-enyl)-5H-dibenzo[a,d]cycloheptene;

3-chloro-5-(3-hydroxy-prop-cis-1-enyl)-5H-dibenzo[a,d]cycloheptene;

5-(3-hydroxy-prop-cis-1-enyl)-3-trifluoromethyl-5H-dibenzo[a,d]cycloheptene;

5-(3-hydroxy-prop-cis-1-enyl)-3-methylmercapto-5H-dibenzo[a,d]cycloheptene;

3-ethylsulfonyl-5-(3-hydroxy-prop-cis-1-enyl)-5H-dibenzo[a,d]cycloheptene;

5-(3-hydroxy-prop-cis-1-enyl)-3-trifluoromethylsulfonyl-5H-dibenzo[a,d]cycloheptene;

3-(N,N-dimethylsulfamoyl)-5-(3-hydroxy-prop-cis-1-enyl)-5H-dibenzo[a,d]cycloheptene;

3-cyano-5-(3-hydroxy-prop-cis-1-enyl)-5H-dibenzo[a,d]cycloheptene;

10,11-dihydro-5-(3-hydroxy-prop-cis-1-enyl)-5H-dibenzo[a,d]cycloheptene;

10,11-dihydro-5-(3-hydroxy-prop-cis-1-enyl)-3-methyl-5H-dibenzo[a,d]cycloheptene;

10,11-dihydro-5-(3-hydroxy-prop-cis-1-enyl)-3-pentyl-5H-dibenzo[a,d]cycloheptene;

10,11-dihydro-5-(3-hydroxy-prop-cis-1-enyl)-3-methoxy-5H-dibenzo[a,d]cycloheptene;

10,11-dihydro-3-ethenyl-5-(3-hydroxy-prop-cis-1-enyl)-5H-dibenzo[a,d]cycloheptene;

10,11-dihydro-3-fluoro-5-(3-hydroxy-prop-cis-1-enyl)-5H-dibenzo[a,d]cycloheptene;

3-chloro-10,11-dihydro-5-(3-hydroxy-prop-cis-1-enyl)-5H-dibenzo[a,d]cycloheptene;
10,11-dihydro-5-(3-hydroxy-prop-cis-1-enyl)-3-trifluoromethyl-5H-dibenzo[a,d]cycloheptene;
10,11-dihydro-5-(3-hydroxy-prop-cis-1-enyl)-3-methylmercapto-5H-dibenzo[a,d]cycloheptene;
10,11-dihydro-3-ethylsulfonyl-5-(3-hydroxy-prop-cis-1-enyl)-5H-dibenzo[a,d]cycloheptene; and
10,11-dihydro-3-N,N-dimethylsulfamoyl-5-(3-hydroxy-prop-cis-1-enyl)-5H-dibenzo[a,d]cycloheptene.

EXAMPLE 4A

This example illustrates methods of preparing the compounds of formula IV trans of the invention. In this example a stirred solution of 0.50 g. of 5-(3-hydroxy-prop-1-ynyl)-5H-dibenzo[a,d]cycloheptene in a mixture of 40 ml. of anhydrous liquid ammonia (redistilled from sodium) and 20 ml. of anhydrous tetrahydrofuran is treated with 0.115 g. of metallic sodium according to the same procedure as described in Example 3A, affording a residue of crude 5-(3-hydroxy-prop-trans-1-enyl)-5H-dibenzo[a,d]cycloheptene which is then further purified by preparative thin-layer chromatography over silica gel employing a 5% acetone-95% benzene (by vol.) mixture as the developing solvent.

Similarly, by following the same procedure as above but using the corresponding products of Preparation 2 as starting materials, the following compounds are respectively prepared:

5-(3-hydroxy-prop-trans-1-enyl)-3-methyl-5H-dibenzo[a,d]cycloheptene;
5-(3-hydroxy-prop-trans-1-enyl)-3-pentyl-5H-dibenzo[a,d]cycloheptene;
5-(3-hydroxy-prop-trans-1-enyl)-3-methoxy-5H-dibenzo[a,d]cycloheptene;
3-fluoro-5-(3-hydroxy-prop-trans-1-enyl)-5H-dibenzo[a,d]cycloheptene;
3-chloro-5-(3-hydroxy-prop-trans-1-enyl)-5H-dibenzo[a,d]cycloheptene;
5-(3-hydroxy-prop-trans-1-enyl)-3-trifluoromethyl-5H-dibenzo[a,d]cycloheptene;
5-(3-hydroxy-prop-trans-1enyl)-3-methylmercapto-5H-dibenzo[a,d]cycloheptene;
3-ethylsulfonyl-5-(3-hydroxy-prop-trans-1-enyl)-5H-dibenzo[a,d]cycloheptene;
5-(3-hydroxy-prop-trans-1-enyl)-3-trifluoromethylsulfonyl-5H-dibenzo[a,d]cycloheptene;
3-(N,N-dimethylsulfamoyl)-5-(3-hydroxy-prop-trans-1-enyl)-5H-dibenzo[a,d]cycloheptene;
3-cyano-5-(3-hydroxy-prop-trans-1-enyl)-5H-dibenzo[a,d]cycloheptene;
10,11-dihydro-5-(3-hydroxy-prop-trans-1-enyl)-5H-dibenzo[a,d]cycloheptene;
10,11-dihydro-5-(3-hydroxy-prop-trans-1-enyl)-3-methyl-5H-dibenzo[a,d]cycloheptene;
10,11-dihydro-5-(3-hydroxy-prop-trans-1-enyl)-3-pentyl-5H-dibenzo[a,d]cycloheptene;
10,11-dihydro-5-(3-hydroxy-prop-trans-1-enyl)-3-methoxy-5H-dibenzo[a,d]cycloheptene;
10,11-dihydro-3-fluoro-5-(3-hydroxy-prop-trans-1-enyl-5H-dibenzo[a,d]cycloheptene;
3-chloro-10,11-dihydro-5-(3-hydroxy-prop-trans-1-enyl)-5H-dibenzo[a,d]cycloheptene;
10,11-dihydro-5-(3-hydroxy-prop-trans-1-enyl)-3-trifluoromethyl-5H-dibenzo[a,d]cycloheptene;
10,11-dihydro-5-(3-hydroxy-prop-trans-1-enyl)-3-methylmercapto-5H-dibenzo[a,d]cycloheptene;
10,11-dihydro-3-ethylsulfonyl-5-(3-hydroxy-prop-trans-1-enyl)-5H-dibenzo[a,d]cycloheptene; and
10,11-dihydro-3N,N-dimethylsulfamoyl-5-(3-hydroxy-prop-trans-1-enyl)-5H-dibenzo[a,d]cycloheptene.

EXAMPLE 5

This example illustrates step 2a of the process. In this example a solution of 3.0 g. of 5-[3-(2-tetrahydropyranyloxy)-prop-cis-1-enyl]-5H-dibenzo[a,d]cycloheptene in 250 ml. of acetone containing 5 ml. of concentrated hydrochloric acid is heated at reflux for 10 minutes, at which time thin-layer chromatographic examination of a reaction aliquot indicates the complete consumption of starting material. The mixture is allowed to cool, then adjusted to pH 6 by the careful addition of aqueous sodium bicarbonate. After most of the acetone is removed by concentration under reduced pressure, the mixture is extracted with methylene chloride. The extracts are washed successively with saturated aqueous sodium bicarbonate and saturated brine, dried over magnesium sulfate and evaporated to dryness under reduced pressure affording a residue of crude 5-(3-hydroxy-prop-cis-1-enyl)-5H-dibenzo[a,d]cycloheptene. Further purification is effected by chromatography on silica gel deactivated by the addition of 10% by weight of water, employing a 25% acetone-75% hexane (vol.) mixture as the eluting solvent.

Similarly, by following the same procedure but respectively using the products of Examples 3 and 3A as starting materials, the corresponding 5-(3-hydroxy-prop-cis-1-enyl)- and 5-(3-hydroxy-prop-trans-1-enyl)-derivatives of formulas (II cis) and (IV trans) are respectively prepared.

EXAMPLE 6

This example illustrates step 3a of the process for preparations of compounds of formulas (II cis) and (IV trans).

To a stirred solution of 0.602 g. of 5-(3-hydroxy-prop-cis-1-enyl)-5H-dibenzo[a,d]cycloheptene in 60 ml. of dry methylene chloride containing 0.6 ml. of triethylamine at −15° to −20°C is added 0.4 ml. of methanesulfonyl chloride in one portion. After stirring for 30 minutes at the same temperature, the mixture is poured into ice water and adjusted to pH 2 by the addition of dilute aqueous hydrochloric acid. The organic phase is separated, washed successively with water and saturated aqueous sodium chloride solution, dried over sodium sulfate, and filtered. The filtrate is evaporated yielding a residue of 5-(3-methanesulfonyloxyprop-cis-1-enyl)-5H-dibenzo[a,d]cycloheptene which is of sufficient purity to be used directly as starting material for the process described in Example 7.

Similarly, by following the same procedure respectively using the products of Examples 4, 4A and 5 as starting material, the corresponding 3-methanesulfonyloxyprop-cis-1-enyl and 3-methanesulfonyloxyprop-trans-1-enyl derivatives are respectively prepared.

EXAMPLE 7

This example illustrates step 4a of the process for preparing compounds of the invention of formulas III cis and V trans. In this example a solution of 1.08 g. of crude 5-(3-methanesulfonyloxyprop-cis-1-enyl)-5H- dibenzo[a,d]cycloheptene in 40 ml. of methylene chloride is treated with 2 ml. of N-β-hydroxyethylpiperazine, and the resulting mixture is stirred for 40 hours at room temperature. The mixture is then treated with 20 ml. of water and sufficient dilute hydrochloric acid to bring the aqueous phase to pH 4–5. After removal of the methylene chloride by evaporation under reduced pressure, the aqueous residue is brought to pH 1 by additional hydrochloric acid and then washed with ethyl ether. The aqueous layer is cooled in an ice bath, made alkaline by careful addition of ammonium hydroxide, and extracted first with ether and then with methylene chloride. The combined organic extracts are washed with saturated brine, dried over sodium sulfate, and evaporated to dryness under reduced pressure to give a residue of 5-[3-(N'-β-hydroxyethyl-N-piperazino)-prop-cis-1-enyl]-5H-dibenzo[a,d]cycloheptene. Further purification is effected by treatment of a methylene chloride-ether solution of the crude amine with a saturated ethereal solution of maleic acid to give a crystalline bis-maleic acid salt.

Similarly, by following the same procedure but respectively using the filtered crude product solutions prepared in Example 6 as starting materials, the corresponding 5-[3-(N'-β-hydroxyethyl-N-piperazino)-prop-cis-1-enyl]- and 5[3-(N'-β-hydroxyethyl-N-piperazino)-prop-trans-1-enyl]- derivatives and their bis-maleic acid salts are respectively prepared.

Similarly, by following the same procedure but respectively using the corresponding products of Example 6, and the appropriate amine reagents, the products prepared in Examples 1 and 2, and their maleic acid salts, are also respectively prepared.

Obviously many modifications and variations of the invention, described herein above and below in the Claims, can be made without departing from the essence and scope thereof.

What is claimed is:
1. A compound selected from the group having the formula:

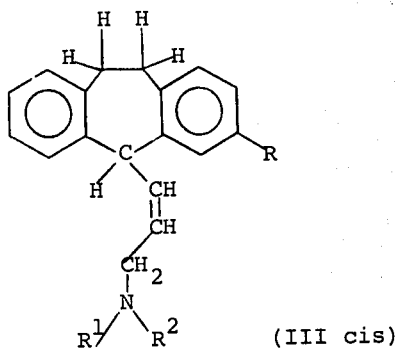

(III cis)

wherein R is hydrogen, chloro, cyano, or trifluoromethyl;
one of R¹ or R² is methyl and the other is selected from the group consisting of hydrogen, methyl, and p-chlorophenacyl;
and pharmaceutically acceptable salts thereof.

2. The compound of claim 1 wherein said compound is selected from the group consisting of 10,11-dihydro-5-(3-[N-methyl-N-(p-chlorophenacyl)]aminoprop-cis-1-enyl)-5H-dibenzo[a,d]cycloheptene and pharmaceutically acceptable salts thereof.

3. The compound of claim 1 wherein said compound is selected from the group consisting of 10,11-dihydro-5-(3-dimethylaminoprop-cis-1-enyl)-5H-dibenzo[a,d]cycloheptene and pharmaceutically acceptable salts thereof.

4. The compound of claim 1 wherein said compound is selected from the group consisting of 10,11-dihydro-5-(3-methylaminoprop-cis-1-enyl)-5H-dibenzo[a,d]cycloheptene and pharmaceutically acceptable salts thereof.

5. The compound of claim 1 wherein said compound is selected from the group consisting of 10,11-dihydro-5-(3-dimethylaminoprop-cis-1-enyl)-3-trifluoromethyl-5H-dibenzo[a,d]cycloheptene and pharmaceutically acceptable salts thereof.

6. The compound of claim 1 wherein said compound is selected from the group consisting of 3-chloro-10,11-dihydro-5-(3-dimethylaminoprop-cis-1-enyl)-5H-dibenzo[a,d]cycloheptene and pharmaceutically acceptable salts thereof.

7. The compound of claim 1 wherein said compound is selected from the group consisting of 3-cyano-10,11-dihydro-5-(3-dimethylaminoprop-cis-1-enyl)-5H-dibenzo[a,d]cycloheptene and pharmaceutically acceptable salts thereof.

* * * * *